(12) United States Patent
Boyaval et al.

(10) Patent No.: US 12,115,360 B2
(45) Date of Patent: Oct. 15, 2024

(54) HYBRID DRUG DELIVERY DEVICES WITH GRIP PORTION

(71) Applicant: AMGEN INC., Thousand Oaks, CA (US)

(72) Inventors: Margaux Frances Boyaval, Newbury Park, CA (US); Brian Stonecipher, Newbury Park, CA (US); Avon Kuo, San Jose, CA (US); James Chan, San Marino, CA (US); Lisa Nugent, Malibu, CA (US)

(73) Assignee: AMGEN INC., Thousand Oaks, CA (US)

( * ) Notice: Subject to any disclaimer, the term of this patent is extended or adjusted under 35 U.S.C. 154(b) by 936 days.

(21) Appl. No.: 17/256,243

(22) PCT Filed: Jul. 22, 2019

(86) PCT No.: PCT/US2019/042749
§ 371 (c)(1),
(2) Date: Dec. 28, 2020

(87) PCT Pub. No.: WO2020/023336
PCT Pub. Date: Jan. 30, 2020

(65) Prior Publication Data
US 2021/0228815 A1    Jul. 29, 2021

Related U.S. Application Data

(60) Provisional application No. 62/702,813, filed on Jul. 24, 2018.

(51) Int. Cl.
*A61M 5/32* (2006.01)
*A61M 5/20* (2006.01)
*A61M 5/31* (2006.01)

(52) U.S. Cl.
CPC ............ *A61M 5/3204* (2013.01); *A61M 5/20* (2013.01); *A61M 2005/2013* (2013.01); *A61M 2005/208* (2013.01); *A61M 2005/3107* (2013.01)

(58) Field of Classification Search
CPC .................. A61M 5/3204; A61M 5/20; A61M 2005/2013; A61M 2005/208; A61M 2005/3107
See application file for complete search history.

(56) References Cited

U.S. PATENT DOCUMENTS

| 7,731,691 B2 * | 6/2010 | Cote ...................... A61M 5/158 |
| | | 604/158 |
| 2003/0229308 A1 * | 12/2003 | Tsals ...................... A61M 5/20 |
| | | 604/116 |

(Continued)

FOREIGN PATENT DOCUMENTS

WO    WO-2018028915 A1    2/2018

OTHER PUBLICATIONS

International Search Report and Written Opinion for International Patent Application No. PCT/US2019/042749, dated Jan. 16, 2020.

*Primary Examiner* — Bradley J Osinski
(74) *Attorney, Agent, or Firm* — MARSHALL, GERSTEIN & BORUN LLP; Michael P. Furmanek

(57) ABSTRACT

Drug delivery devices are described that provide hybrid forms with gripping and stability functionalities, such as a grip portion on a skin contact surface. In some versions, the drug delivery devices can include a cep having a release liner such that removal of the cap exposes the grip portion. In some versions, the drug delivery devices include a retractable needle guard having the grip portion extending therearound.

20 Claims, 8 Drawing Sheets

(56) References Cited

U.S. PATENT DOCUMENTS

| | | |
|---|---|---|
| 2009/0048578 A1 | 2/2009 | Adams et al. |
| 2011/0040280 A1 | 2/2011 | Ijitsu et al. |
| 2012/0253314 A1 | 10/2012 | Harish et al. |
| 2015/0258284 A1* | 9/2015 | Fenster ............... A61M 5/3205 604/115 |

* cited by examiner

HYBRID DRUG DELIVERY DEVICES WITH GRIP PORTION

CROSS-REFERENCE TO RELATED APPLICATION

This is the United States National Phase of International Patent Application No. PCT/US19/42749, filed Jul. 22, 2019, which claims priority to U.S. Provisional Patent Application No. 62/702,813, filed Jul. 24, 2018, the entire contents of each of which are hereby incorporated by reference herein.

FIELD OF THE DISCLOSURE

The present disclosure generally relates to drug delivery devices.

BACKGROUND

Drugs can be administered through the use of drug delivery devices such as autoinjectors or on-body injectors. Autoinjectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological barriers, form factors, or ergonomic considerations.

Even after receiving specified training in the use of such devices, however, some patients and/or caregivers can experience challenges while using autoinjectors and/or on-body injectors. Such challenges may relate to placement of the device on the person, holding the device during an injection operation, and/or removing the device after use. Specifically, conventional autoinjectors can have an elongate, high-profile housing that requires a user to position and hold the housing through an entire injection operation without additional aid.

SUMMARY

In accordance with some example aspects, drug delivery devices are provided that include a housing that has a generally vertical orientation along a longitudinal axis and drug delivery components, including a needle, that are disposed within the housing such that at least a plurality of the drug delivery components are disposed in a generally stacked relation along the longitudinal axis. The drug delivery devices further include a generally planar skin contact surface extends around the needle and a retention portion of the skin contact surface is configured to grip skin of a user.

According to some forms, the drug delivery devices can further include a needle guard that is coupled to the housing and is movable between a guard position and a use position. The needle guard includes a needle opening that extends therethrough such that moving the needle guard to the use position causes the needle to extend through the needle opening.

According to some forms, the needle guard can include a bottom wall defining at least a portion of the skin contact surface.

According to some forms, the bottom wall can have a dimension that extends thereacross that is between about one half and a full height of the housing along the longitudinal axis, such that the housing is stable in a vertical orientation with the housing resting on a horizontal surface.

According to some forms, the bottom wall can include a flange that extends outwardly from adjacent portions of the needle guard.

According to some forms, the retention portion can include an annular retention portion that extends around the needle opening.

According to some forms, an outer edge of the retention portion can be spaced inwardly from an outer edge of the skin contact surface.

According to some forms, the drug delivery devices can further include a cap having a bottom wall and a sidewall that extends upwardly from the bottom wall, where the bottom wall includes a surface that is configured to engage the retention portion with the cap coupled to at least one of the needle guard or housing and provide a release liner for the retention portion during removal of the cap.

In some forms, the cap can be made of a flexible material and the sidewall can include an inwardly projecting portion that is configured to engage an edge of the bottom wall.

In some forms, the sidewall can be sized to extend along the needle guard in a direction generally parallel to the longitudinal axis to engage the housing.

In some forms, the cap can include a needle shield that extends upwardly from the bottom wall and configured to project through the needle opening.

In some forms, the housing can have an inverted frusto-conical configuration with an annular cross-section extending perpendicular to the longitudinal axis, a downwardly tapering sidewall, and a top wall.

In some forms, the housing can include a cylindrical proximal end adjacent to the needle guard and a generally box-shaped distal end.

In some forms, the housing can include a window portion that extends across a top of the distal end to sides thereof to provide visibility to the drug delivery components disposed within the housing.

According to some forms, the housing includes a downwardly oriented housing opening having the needle guard extending therethrough and the skin contact surface is a bottom surface of the housing extending around the housing opening.

In some forms, the housing can include a rounded proximal end that extends to the bottom surface such that the housing opening has a smaller cross-section area in a direction perpendicular to the longitudinal axis than adjacent portions of the housing.

In some forms, the housing can include a grip that is formed by an opening that extends transversely through at least a portion of the housing.

In some forms, the housing can include an annular window that provides visibility to the drug delivery components disposed within the housing.

In some forms, the housing includes a base wall that is disposed adjacent to and at an angle with respect to the housing opening such that the housing is configured to be pivoted from resting on the base wall to engage a desired portion of skin with the needle guard to thereby retract the needle guard and bring the skin contact surface into engagement with the skin.

In some forms, the device can include a cap with a bottom wall and a sidewall that extends upwardly from the bottom wall, where the sidewall is sized to couple to the housing with the retention portion spaced from the cap and the needle guard in an guard position.

In some forms, the retention portion of any of the disclosed drug delivery devices can include an adhesive layer.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

Figure 2:
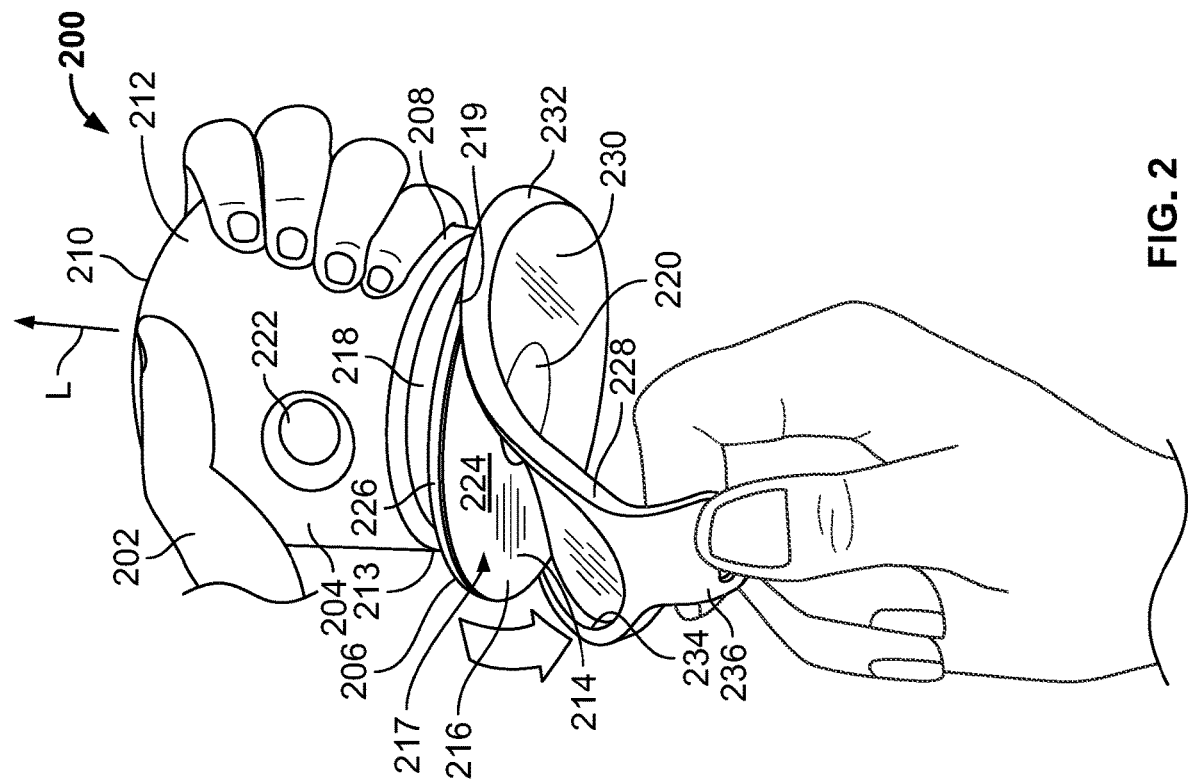
FIG. 2 is a perspective view of a first example drug delivery device in accordance with various embodiments.

The examples disclosed herein relate to delivery devices referred to as autoinjectors or hybrid autoinjectors that are structured to fit the lifestyle of some users better than some known and conventional autoinjectors or wearable on-body injector devices. For example, a user can choose to perform an injection procedure using the example delivery devices hands-free by temporarily adhering a delivery device to their body or in an assisted manner that may still require some manual holding of the device. The delivery devices can include a gripping aid for positioning and holding the devices against an intended portion of skin to stabilize the delivery device relative to the body when an injection procedure is being performed. In the former examples, the gripping aid can be an adhesive that extends over a relatively small area relative to conventional devices so that subsequent removal of the device from the skin has correspondingly reduced effects, (e.g., pain). In the latter examples, the gripping aid can utilize a reduced strength adhesive so that the devices can provide aid to a user holding the device rather than being capable of hands-free operation. The gripping aid can alternatively utilize a non-adhesive tacky material and/or textured surface.

The example delivery devices can be structured to be easily held by a user with dexterity or strength challenges to substantially ensure that the injection completes successfully by increasing the grip and/or handle size of the delivery device. Put another way, the form factor of the disclosed delivery devices are structured to be more easily held in place against the skin during an injection procedure. Furthermore, because the form factor of the disclosed examples is different than some known delivery devices, users may feel less stigma using the example devices because the delivery devices may be less recognizable as a drug delivery device.

Additionally or alternatively, the example delivery devices are structured to increase a foot print and/or increase the surface area interacting with the skin of the user during an injection procedure to increase stability of the delivery device. As such, the examples disclosed herein enable less adhesive, reduced strength adhesive and/or no adhesive to be used when stabilizing the delivery devices relative to the skin. Reducing and/or eliminating the use of adhesives is especially beneficial for users with thin skin or other skin issues where adhesives may cause negative reactions (e.g., pain, a rash).

In some versions, the drug delivery devices have generally co-axial or stacked drug delivery components such that some or all of a drug reservoir, plunger mechanism, and needle are axially aligned or have components disposed above one another in an operative orientation. The drug delivery devices described herein having this configuration provide stability, gripping, and/or adhesion functionalities typically associated with low profile drug delivery devices to aid users in orienting and supporting the device during an injection operation. As a more specific example, drug delivery devices of this form include a housing for the co-axial or stacked drug delivery components having a skin contact surface that extends generally transverse to the longitudinal axis of the housing. The skin contact surface can advantageously be utilized to support one or more retention materials that can aid a user in holding the device on the skin. The retention materials can be any non-slip texture or material, and/or adhesive.

The devices can include a cap that removably couples to the housing to cover the retention material prior to use. In some versions, the cap can act as a release liner for the retention materials or have a release liner attached thereto, so that removal of the cap also causes the release liner to be removed. In other versions, the cap can be spaced from the retention materials. Regardless, upon removal of cap the retention material is exposed to be brought into contact with the user's skin.

Figure 1:
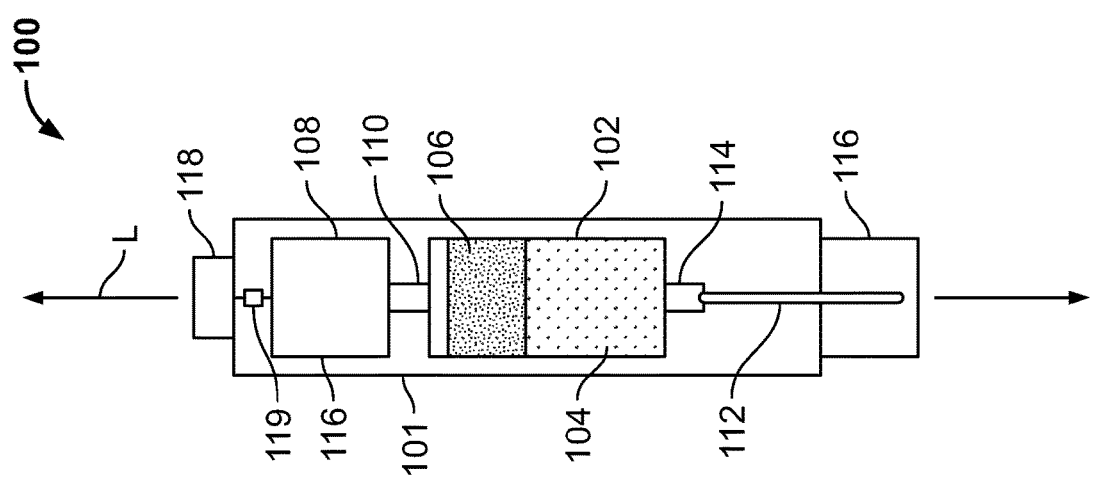
FIG. 1 is a diagrammatic view of an autoinjector drug delivery device in accordance with various embodiments.
Figure 3:
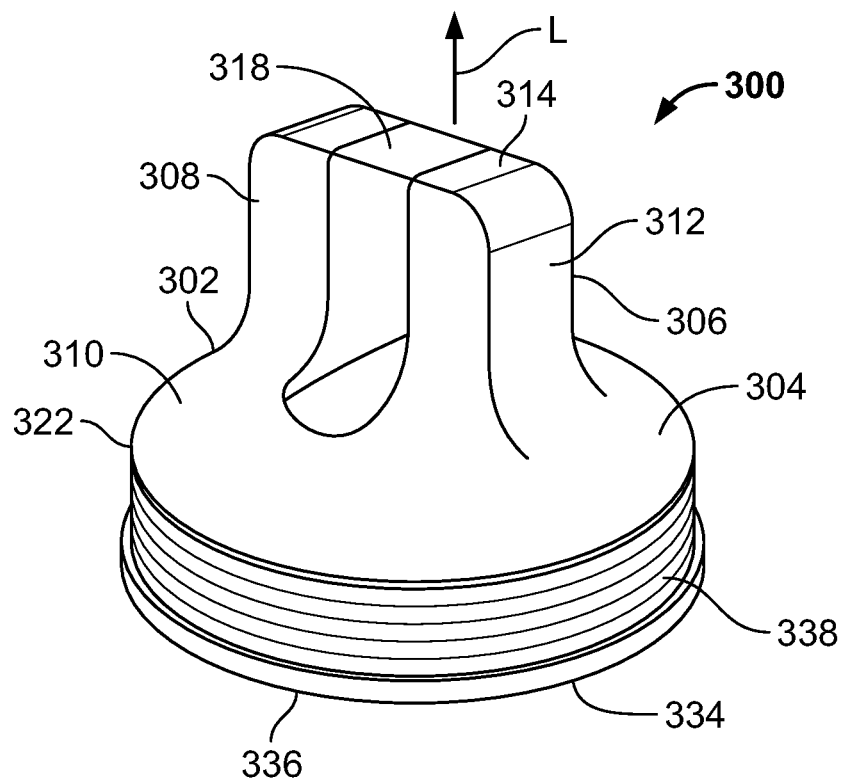
FIG. 3 is a perspective view of a second example drug delivery device in accordance with various embodiments.

In some versions as illustrated in FIG. 1, drug delivery devices 100, such as autoinjectors, can have a vertically oriented configuration with some or all drug delivery components disposed in stacked relation along a longitudinal axis L within a housing 101 of the devices 100. As a more specific example, the devices 100 can be configured to operate and inject a user with the device 100 oriented generally perpendicular to a skin surface of the user. The drug delivery components can include a reservoir 102 having a drug 104 contained therein, a stopper 106 disposed within the reservoir 102 and slidably movable therein along the longitudinal axis L, a drive mechanism 108 coupled to a plunger 110 to drive the stopper 106 through the reservoir 102, a needle 112 oriented along the longitudinal axis L, a flow path 114 fluidly coupling the reservoir 102 to the needle 112, and a needle insertion mechanism 116 configured to insert the needle 112 to a desired subcutaneous depth within the user. By some approaches, the needle insertion mechanism 116 can be a retractable needle guard to expose the needle 112 or a drive mechanism to longitudinally move the needle a desired distance. For example, the drive mechanism 108 can be configured to drive both movement of the stopper 106 and the needle 112 by moving some or all of the reservoir 102, flowpath 114, and needle 112. As commonly configured, one or more of the components of the device 100, such as the drive mechanism 108 and needle insertion mechanism 116, can be operable in response to actuation of a user input device 118 accessible on an exterior of the housing 101. Suitable drive mechanisms include, but are not limited to, springs, gas sources, phase changing materials, motors, or other electromechanical systems. Pursuant to this, the device 100 can include electronic components, such as a controller 119, to control operation of one or more of the drug delivery components. It will be understood that although FIG. 1 shows all of the components centered along the longitudinal axis L, one or more of the components can be disposed off-center from the longitudinal axis L within the housing 101 and still be considered to be in a stacked relation. In one example, an autoinjector drug delivery device having drug delivery components in a stacked relation corresponds to the reservoir 102 co-axially aligned with the needle 112. Example autoinjector devices are described in U.S. Ser. No. 62/447,174, filed Jan. 17, 2017, which is hereby incorporated by reference herein.

Given the stacked orientation of the components and the high-profile nature of the housing 101, the devices 100 of these versions can be prone to have a physically unstable configuration (i.e., prone to tipping over unless held by a user), relying on a user to position, orient, and hold the device 100 during an injection operation. Advantageously, devices described herein with reference to FIGS. 2 to 12, have a hybrid functionality providing aid to a user for more stability with a stable vertical orientation. Further, the devices can have a grip portion of the contact surface so that the devices grip the user's skin to provide aid to users to position and hold the device 100 during an injection operation.

One example embodiment of an autoinjector device 200 providing these features is shown in FIG. 2. The device 200 includes a vertically oriented housing 202 oriented along a longitudinal axis L. The housing 202 has a downwardly tapered sidewall 204 that extends between a proximal end 208 and a top wall 210 at a distal end 212.

As shown in FIG. 2, the device 200 includes a needle guard 206 that extends downwardly from the proximal end 208 of the housing 202 to protect against inadvertent contact with the needle (not shown). The needle guard 206 is retractable into the housing 202 and/or compressible, being made of a compressible material or having a structure configured to collapse, to expose the needle during an injection operation. The needle guard 206 can also be biased to the extended position by a spring or the like so that the guard 206 covers the needle when the device 200 is not pressed against a surface.

Retraction of the needle guard 206 can operate as an actuation to cause the drug delivery components within the housing 202 to operate as described above with respect to FIG. 1. Alternatively, the device 200 can have a separate user input device that is accessible on an exterior of the housing 202. In the illustrated form, the needle guard 206 is cylindrical with a diameter spaced inwardly from an edge 213 of the proximal end 208 of the housing 202 to allow the needle guard 206 to be retracted into the housing 202.

The needle guard 206 includes a bottom wall 214 that provides a planar skin contact surface 216 for the device 200 for positioning on a user. In contrast to some conventional devices, the skin contact surface 216 has a dimension, e.g., circumference, extending thereacross that is at least half a height of the sidewall 204 and, in some forms, about two thirds of a height of the sidewall 204.

In the illustrated form, the bottom wall 214 includes a flange 217 that extends outwardly from a neck portion 218 of the needle guard 206 such that the skin contact surface 216 has a greater perimeter than a perimeter of the proximal end 208 of the sidewall 204. Further, the flange 217 and tapered sidewall 204 gives the device 200 a top hat shaped configuration providing an ergonomic shape with a waisted retention portion 219 for a user to hold the skin contact surface 214 against a desired portion of the skin. In the illustrated form, the sidewall 204 has an annular cross-section giving the housing a frusto-conical shape.

As shown in FIG. 2, the bottom wall 214 includes a needle opening 220 extending through a central portion thereof to provide access for a needle (not shown) to be driven therethrough during an injection operation. Further, the housing 202 can include a window 222 to allow a user to view drug delivery components within the housing 202, such as the reservoir, stopper, plunger, and needle (not shown).

To aid a user in positioning and holding the device 200 against a desired portion of skin, a retention portion 224 of the skin contact surface 216 has an annular configuration and extends around the needle opening 220 to cover some or all of the skin contact surface 216. In the illustrated form, the retention portion 224 extends between a perimeter 226 of the bottom wall 214 and the needle opening 220. The retention portion 224 can be any suitable gripping material and/or textured surface. For example, the retention portion 224 can be a coating, layer, or tape, and can be an adhesive, a non-slip elastomer, such as silicone, rubber, etc.

The device 200 further includes a cap 228 that removably couples to the bottom wall 214 to cover the skin contact surface 216 and the retention portion 224 thereon prior to use. The cap 228 includes a planar wall 230 having a shape complementary to the bottom wall 214 and an upwardly extending sidewall 232 having an inward slant or inwardly projecting lip 234 that is configured to project above the flange 217 to secure the cap 228 to the bottom wall 214. In some versions, the cap 228 can include a gripping tab 236 and can be made of a flexible material so that a user can peel the cap 228 back to remove the cap 228 from the housing 202. Further, the cap 228 can be made of a material configured to easily release from the retention portion 224, such that the cap 228 can act as a release liner for the device 200.

Another example embodiment of an autoinjector device 300 providing the above features is shown in FIGS. 3 to 7. The device 300 includes a vertically oriented housing 302 oriented along a longitudinal axis L. The housing 302 includes a cylindrical proximal end 304 oriented toward a user and a generally box-shaped distal end 306. As shown, the housing 302 can include rounded transitional portions extending between the proximal and distal ends 304, 306. The distal end 306 provides a gripping tab for a user to hold and position the device 300 on a desired portion of skin. In the illustrated form, the distal end 306 has a rectangular cross-section with side walls 308 extending across an intermediate portion of the proximal end 304 to adjacent a perimeter 310 thereof, end walls 312 extending between the side walls 308, and a top wall 314.

If desired, the housing 302 can include a window 318 to allow a user to view drug delivery components within the housing 302, such as the reservoir, stopper, plunger, and needle (not shown). In the illustrated form, the window 318 extends up one of the side walls 308, across the top wall 314, and down the other of the side walls 308 providing visibility from the sides and the top of the device 300.

Figure 5:
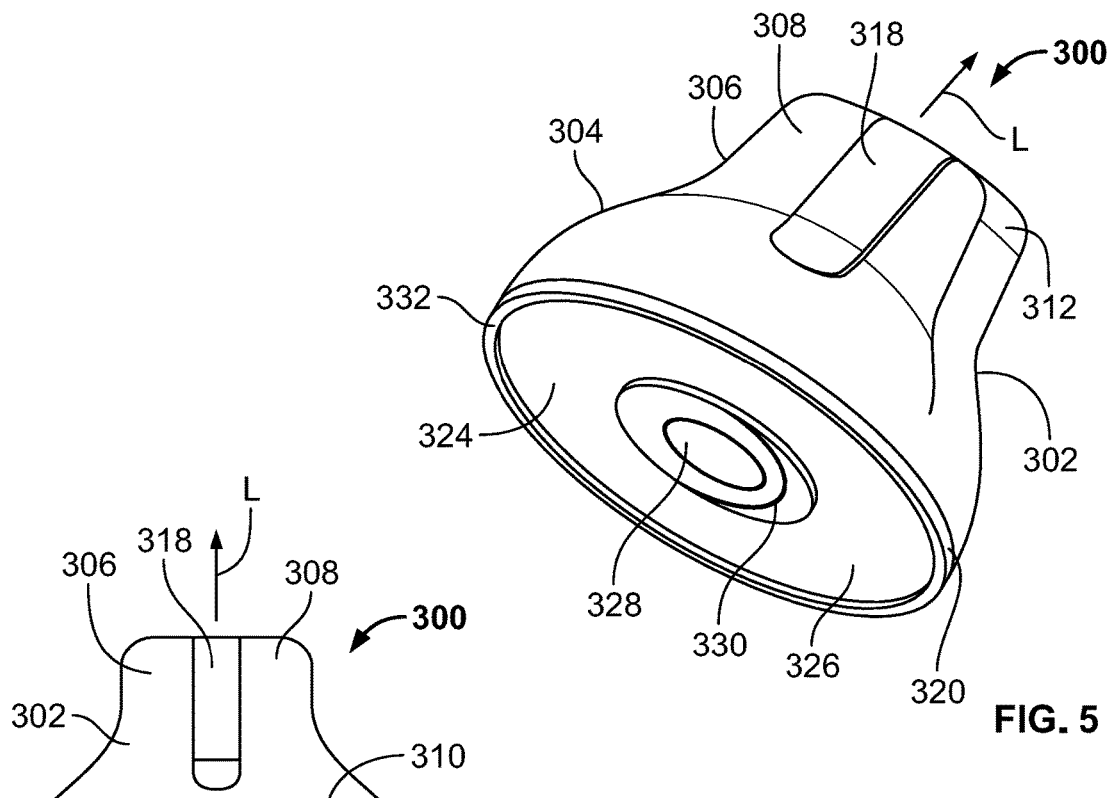
FIG. 5 is a bottom perspective view of the drug delivery device of FIG. 3 with a cap removed.
Figure 6:
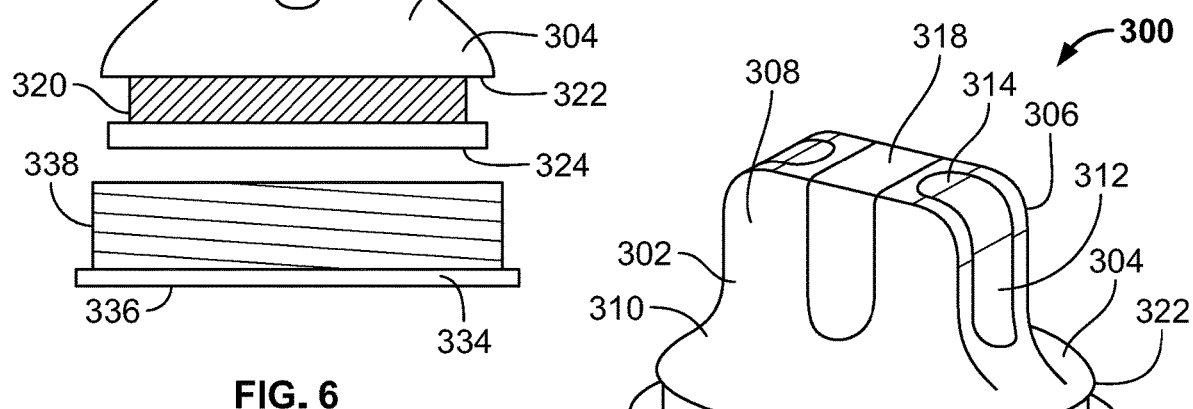
FIG. 6 is an side exploded view of the drug delivery device of FIG. 3.
Figure 7:
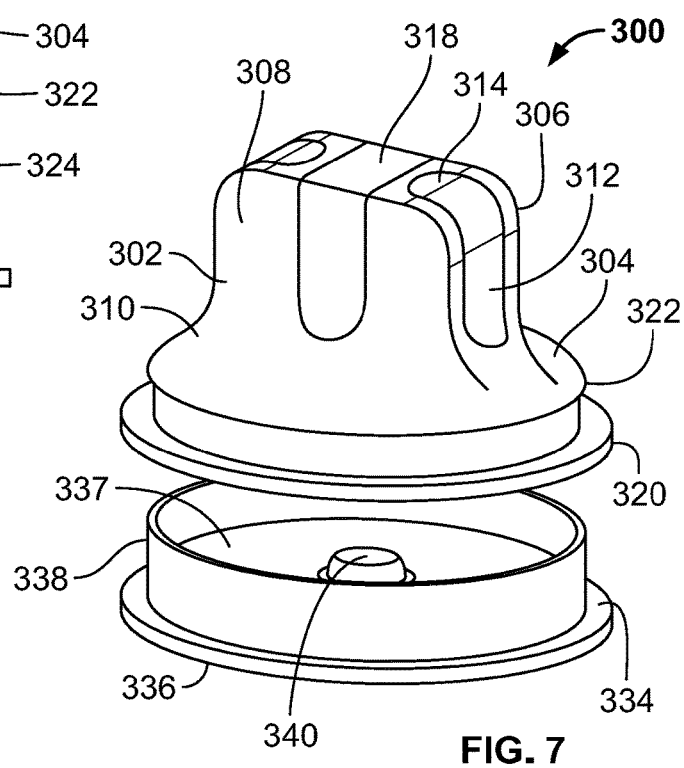
FIG. 7 is a perspective exploded view of the drug delivery device of FIG. 3.

As shown in FIGS. 5 to 7, the device 300 includes a needle guard 320 that extends downwardly from the proximal end 304 of the housing 302 to protect against inadvertent contact with the needle (not shown). The needle guard 320 is retractable into the housing 302 and/or compressible, being made of a compressible material or having a structure configured to collapse, to expose the needle during an injection operation. The needle guard 320 can also be biased to the extended position by a spring or the like so that the guard 320 covers the needle when the device 300 is not pressed against a surface.

Retraction of the needle guard 320 can operate as an actuation to cause the drug delivery components within the housing 302 to operate as described above with respect to FIG. 1. Alternatively, the device 300 can have a separate user input device that is accessible on an exterior of the housing 302. In the illustrated form, the needle guard 320 is cylindrical with a diameter spaced inwardly from an edge 322 of the proximal end 304 of the housing 302 to allow a cap to be secured thereover, as discussed in more detail below.

The needle guard 320 includes a bottom wall 324 that provides a planar skin contact surface 326 for the device 300 for positioning on a user. In contrast to some conventional devices, the skin contact surface 326 has a dimension, e.g., circumference, extending thereacross that is at least half a height of the housing 302 and, in some forms, about the same as a height of the housing 302.

A needle opening 328 extends through a central portion of the bottom wall 324 to provide access for the needle to be driven therethrough during an injection operation. To aid a user in positioning and holding the device 300 against a desired portion of skin, a retention portion 330 extends around the opening 328 to cover some or all of the skin contact surface 326. In the illustrated form, the retention portion 330 has an annular configuration and extends less than half of a radial dimension of the bottom wall 324 to be spaced from a perimeter 332 thereof. The retention portion 330 can be any suitable gripping material and/or textured surface. For example, the retention portion 330 can be a coating, layer, or tape, and can be an adhesive, a non-slip elastomer, such as silicone, rubber, etc.

As shown in FIGS. 6 and 7, a cap 334 for the device 300 includes a bottom wall 336 and a side wall 338 upstanding from the bottom wall 336. The bottom wall 336 and side wall 338 define an interior sized to receive the needle guard 326 therein in an unretracted or uncompressed state when the cap 334 is secured to the housing 302. The cap 334 can removably secure to the housing 302 by any suitable mechanism, such as snap-fit, friction fit, threading, etc. The bottom wall 336 is configured to cover the skin contact surface 326 and engage the retention portion 330 thereon prior to use. Pursuant to this, the bottom wall 336 can have a release liner 337 adhered or otherwise attached thereto so that removal of the cap 334 also removes the release liner 337. Alternatively, the bottom wall 336 can be made of a material configured to easily release from the retention portion 330, such that the cap 334 can act as a release liner for the device 300.

The cap 334 can further include a needle shield 340 that projects upwardly from the bottom wall 336 and is sized and configured to extend through the needle opening 328 to engage the needle when the cap 334 is secured to the housing 302. The needle shield 340 can protect the needle during storage and transportation. If desired, the cap 334 can maintain sterility within the device 300 and/or the needle can be embedded within the needle shield 340 to maintain closed container integrity (CCI) prior to an initial removal of the cap 334. In some versions, the needle shield 340 can have a funneled upper surface to locate and direct the needle into a desired orientation when the needle shield 340 is inserted through the opening 328. In an alternative form, the needle shield 340 can instead couple to a needle shield preinstalled in the device 300, such that removal of the cap 334 also removes the separate needle shield.

Figure 8:
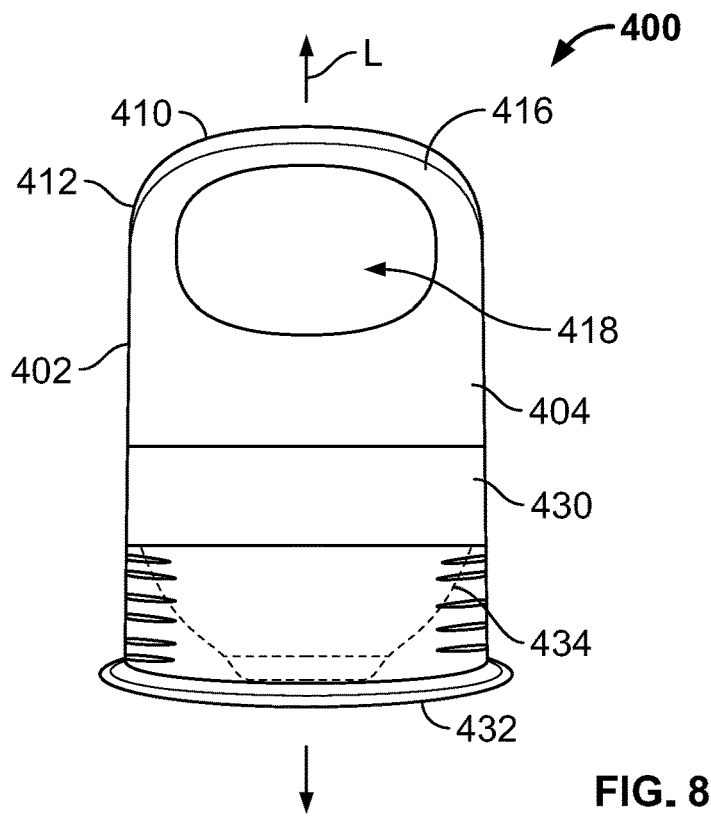
FIG. 8 is a front elevational view of a third example drug delivery device in accordance with various embodiments.
Figure 9:
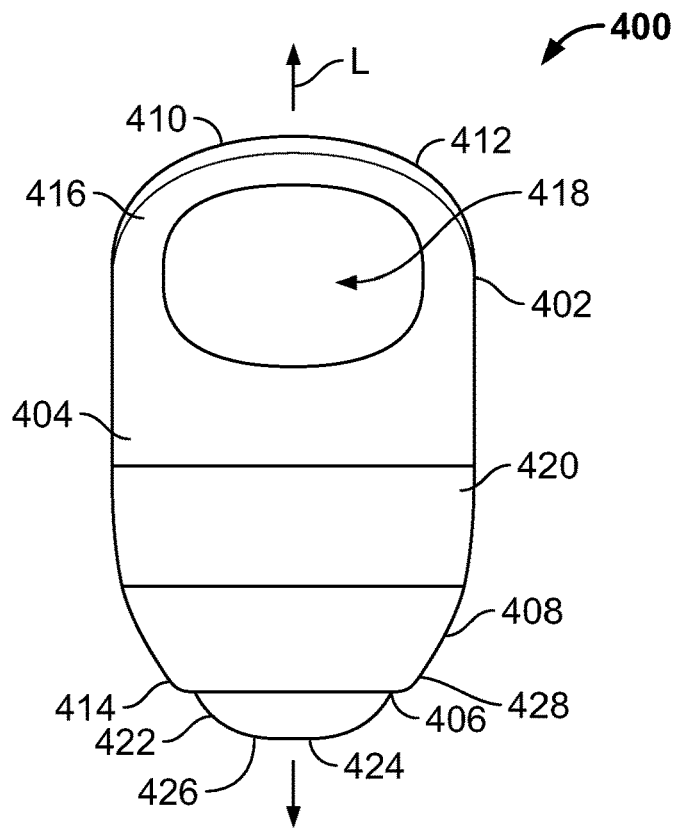
FIG. 9 is a front elevational view of the drug delivery device of FIG. 8 with a cap removed.
Figure 10:
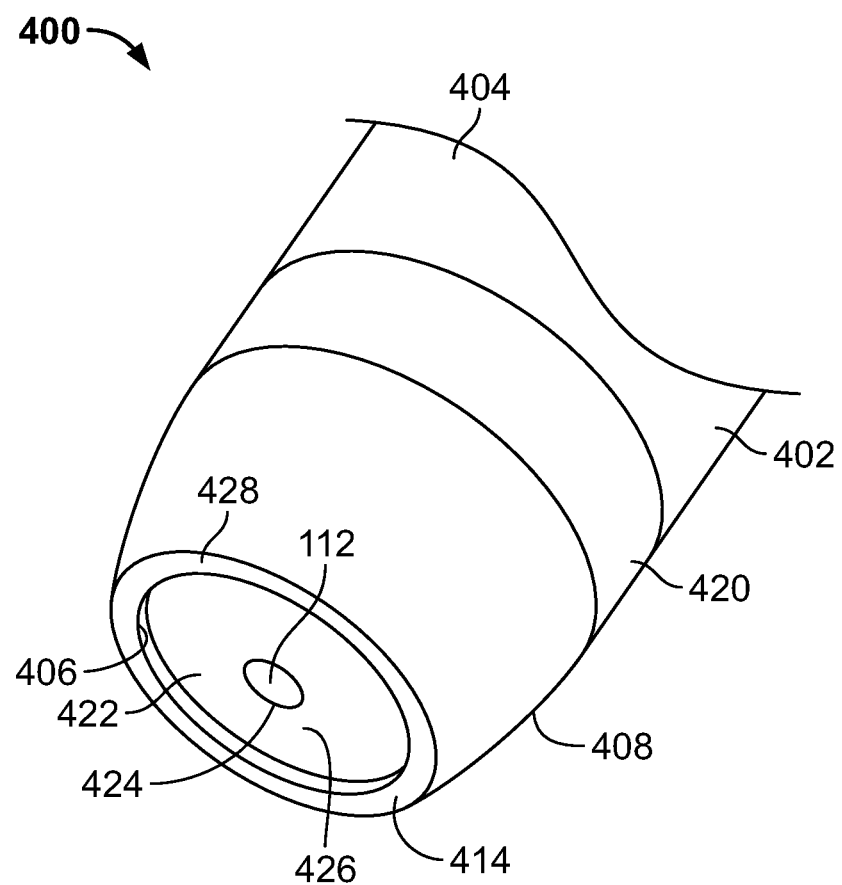
FIG. 10 is a sectional perspective view of the drug delivery device of FIG. 8 with a cap removed and a needle shield retracted.

Another example embodiment of an autoinjector device 400 providing the above features is shown in FIGS. 8 to 10. The device 400 includes a vertically oriented housing 402 oriented along a longitudinal axis L. The housing 402 includes a tubular sidewall 404 that extends between an open bottom 406 at a proximal end 408 and a top wall 410 at a distal end 412. In some forms, the tubular sidewall 404 can have a pill-shaped or oval cross-section. As shown, the sidewall 404 can have a bulleted or tapered profile at the proximal end 408 such that the open bottom 406 has a smaller cross-section than other portions of the housing 402. The open bottom 406 provides an annular skin contact surface 414 (FIG. 10) for positioning on a user. In contrast to some conventional devices, opposing portions of the skin contact surface 414 have a dimension extending therebetween that is at least about 0.25 of a height of the sidewall 404.

In the illustrated form, the sidewall 404 can include a handle 416 at the distal end 412 formed by an opening 418 extending horizontally through the housing 402 in a direction perpendicular to the longitudinal axis L. The handle 416 provides a convenient structure for a user to hold the device 400, grasp to pull off a cap, described below, push the housing 402 onto a desired portion of skin, and pull the housing 402 off the skin.

If desired, the housing 402 can include a window 420 to allow a user to view drug delivery components within the housing 402, such as the reservoir, stopper, plunger, and needle (not shown). In the illustrated form, the window 420 extends around the sidewall 404 with portions extending generally parallel to the longitudinal axis L to provide 360 degrees of visibility into the housing 402.

As shown in FIG. 9, the device 400 includes a needle guard 422 that extends downwardly through the open bottom 406 of the housing 402 to protect against inadvertent contact with the needle (FIG. 10). The needle guard 422 is retractable into the housing 402 and defines a needle opening 424 at an end 426 thereof to expose the needle for an injection operation. The needle guard 422 can also be biased to the extended position by a spring or the like so that the guard 422 covers the needle when the device 400 is not pressed against a surface. In alternative versions, the needle guard 422 can be made of a compressible material or having a structure configured to collapse.

Retraction of the needle guard 422 can operate as an actuation to cause the drug delivery components within the housing 402 to operate as described above with respect to FIG. 1. Alternatively, the device 400 can have a separate user input device that is accessible on an exterior of the housing 402. In the illustrated form, the needle guard 422 has a rounded profile that is generally complementary to the profile of the proximal end 408.

To aid a user in positioning and holding the device 400 against a desired portion of skin, a retention portion 428 is disposed on the skin contact surface 414. The retention portion 428 can be any suitable gripping material and/or textured surface. For example, the retention portion 428 can be a coating, layer, or tape, and can be an adhesive, a non-slip elastomer, such as silicone, rubber, etc. To use the device 400, a user positions the housing 402 above the skin and presses downwardly to retract the needle guard 422 into the housing 402. Retraction of the needle guard 422 into the housing 402 causes the needle to insert to a desired subcutaneous depth and brings the retention portion 428 into engagement with the skin. The grip of the retention portion 428 aids a user in holding the device 400 in the desired orientation and location during the injection operation.

As shown in FIG. 8, the device 400 can include a cap 430 that includes a bottom wall 432 and a side wall 434 upstanding from the bottom wall 432. The side wall 434 has a cross-section complementary to the housing 402 and has a height to engage the sidewall 404 above the bulleted proximal end 408 and the retention portion 428. The cap 430 preferably engages the sidewall 404 so that the needle guard 422 is maintained in an extended position within an interior of the cap 430. The cap 430 can removably secure to the housing 402 by any suitable mechanism, such as snap-fit, friction fit, etc.

Another example embodiment of an autoinjector device 500 providing the above features is shown in FIGS. 11 to 14. The device 500 includes a vertically oriented housing 502 oriented along a longitudinal axis L. The housing 502 includes a plurality of walls defining an interior sized to receive drug delivery components as described above with respect to FIG. 1. In the illustrated form, the housing 502 includes opposing main walls 504 having a domed configuration with a curved top edge 506 and a bottom edge 508, a top wall 510 extending between the main walls 504 over the curved top edge 506, a base wall 512 extending between the main walls 504 along a first portion 514 of the bottom edge 508. The housing 502 further includes a rectangular mouth 516 defined on two opposing sides by edges of the top wall 510 and base wall 512 and on the other two opposing sides by second portions 518 of the bottom edge 508 angled upwardly with respect to the first portion 514. So configured, with the housing 502 resting on the base wall 512, the mouth 516 extends upwardly from the base wall 512 at an angle with respect thereto.

The portions of the main, top, and base walls 504, 510, 512 defining the mouth 516 provide a rectangular frame skin contact surface 520 (FIG. 13) for positioning on a user during an injection operation. In contrast to some conventional devices, opposing portions of the skin contact surface 520 have a dimension extending therebetween that is at least about 0.25 of a height of the housing 502 and, in some forms, at least about 0.5 of a height of the housing 502.

If desired, the housing 502 can include a window 522 to allow a user to view drug delivery components within the housing 502, such as the reservoir, stopper, plunger, and needle (not shown). In the illustrated form, the window 522 extends from one of the main walls 504 to the other of the main walls 504 over the top wall 510. This configuration provides a user with visibility into the housing 502 from multiple directions.

Figure 11:
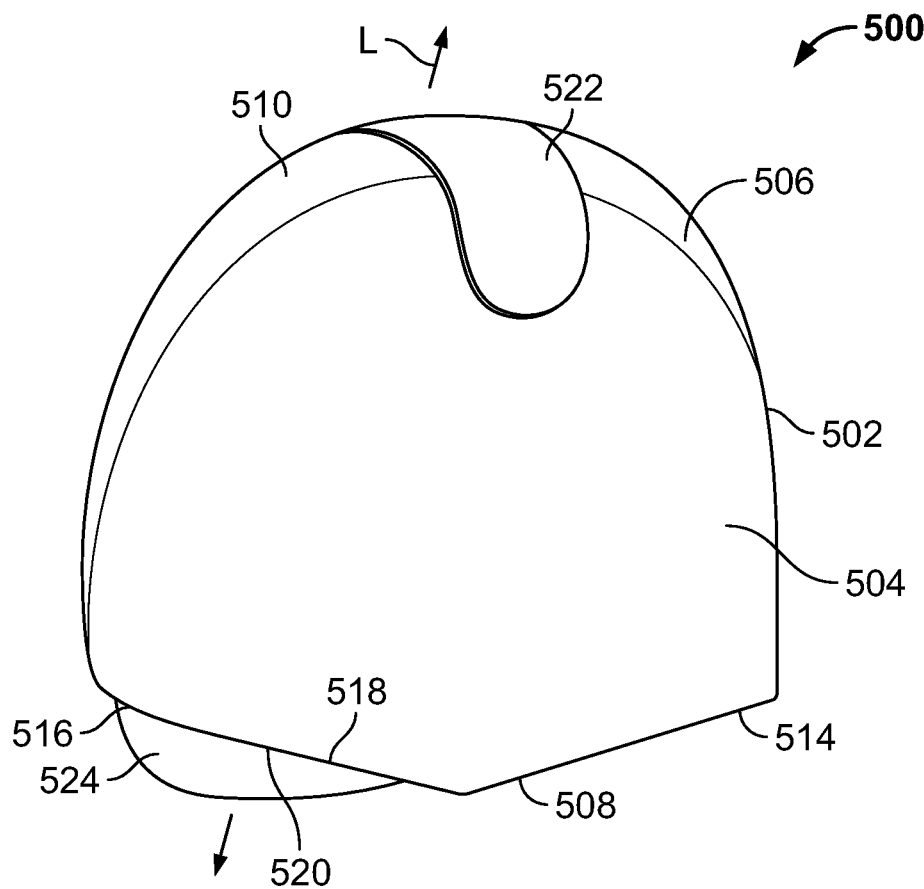
FIG. 11 is a perspective view of a fourth example drug delivery device in accordance with various embodiments.
Figure 12:
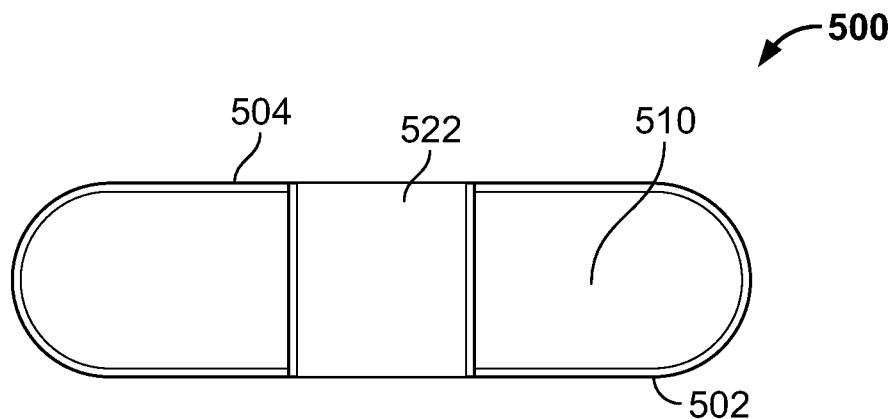
FIG. 12 is a top plan view of the drug delivery device of FIG. 11.
Figure 13:
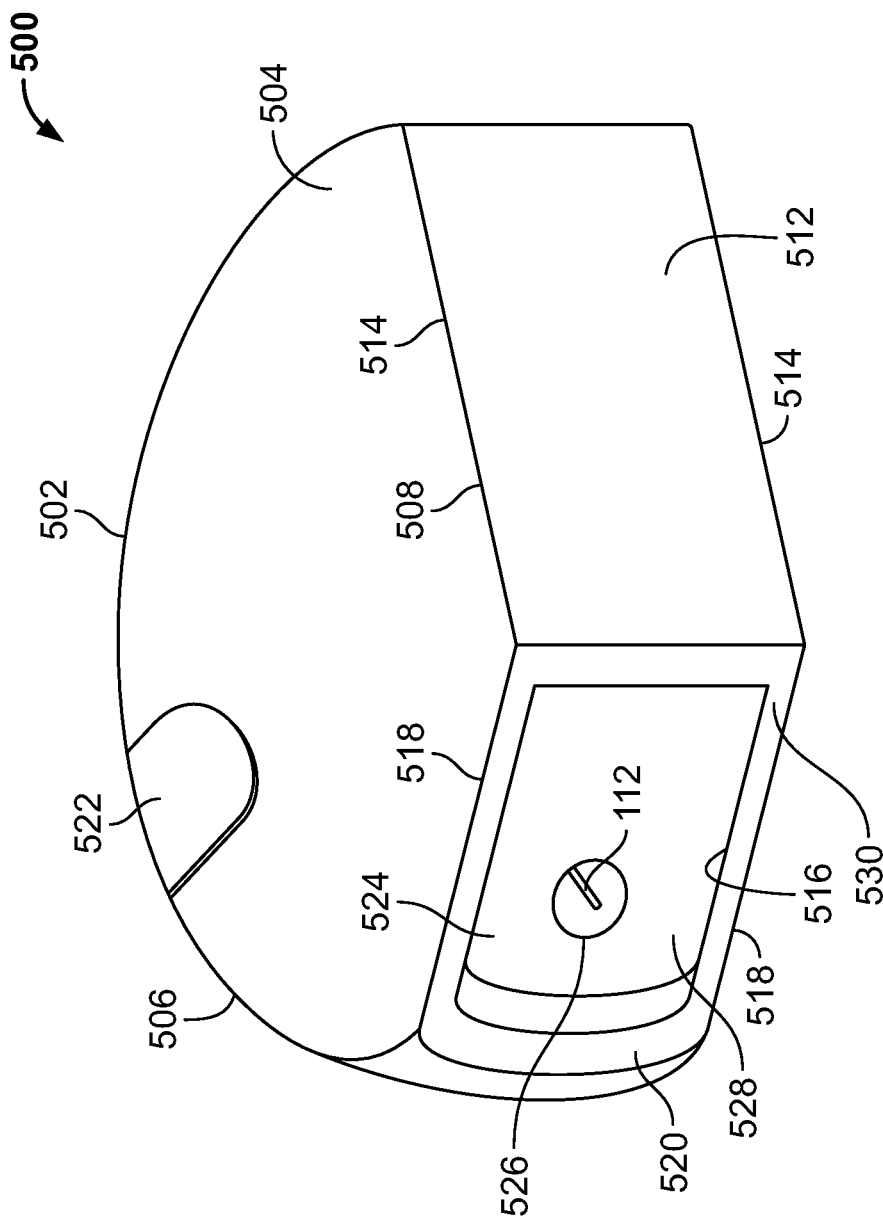
FIG. 13 is a bottom perspective view of the drug delivery device of FIG. 11.

As shown in FIG. 11, the device 500 includes a needle guard 524 that extends through the mouth 516 of the housing 502 to protect against inadvertent contact with the needle (FIG. 13). The needle guard 524 is retractable into the housing 502 and defines a needle opening 526 (FIG. 13) at an end 528 thereof to expose the needle for an injection operation. The needle guard 524 can also be biased to the extended position by a spring or the like so that the guard 524 covers the needle when the mouth 516 of the device 500 is not pressed against a surface. In alternative versions, the needle guard 524 can be made of a compressible material or having a structure configured to collapse.

Retraction of the needle guard 524 can operate as an actuation to cause the drug delivery components within the housing 502 to operate as described above with respect to FIG. 1. Alternatively, the device 500 can have a separate user input device that is accessible on an exterior of the housing 502. In the illustrated form, when extended, the needle guard 522 has a wedge shaped profile generally following the dome shaped configuration of the main walls 504.

To aid a user in positioning and holding the device 400 against a desired portion of skin, a retention portion 530 is disposed on the skin contact surface 520. The retention portion 530 can be any suitable gripping material and/or textured surface. For example, the retention portion 530 can be a coating, layer, or tape, and can be an adhesive, a non-slip elastomer, such as silicone, rubber, etc.

Figure 14:
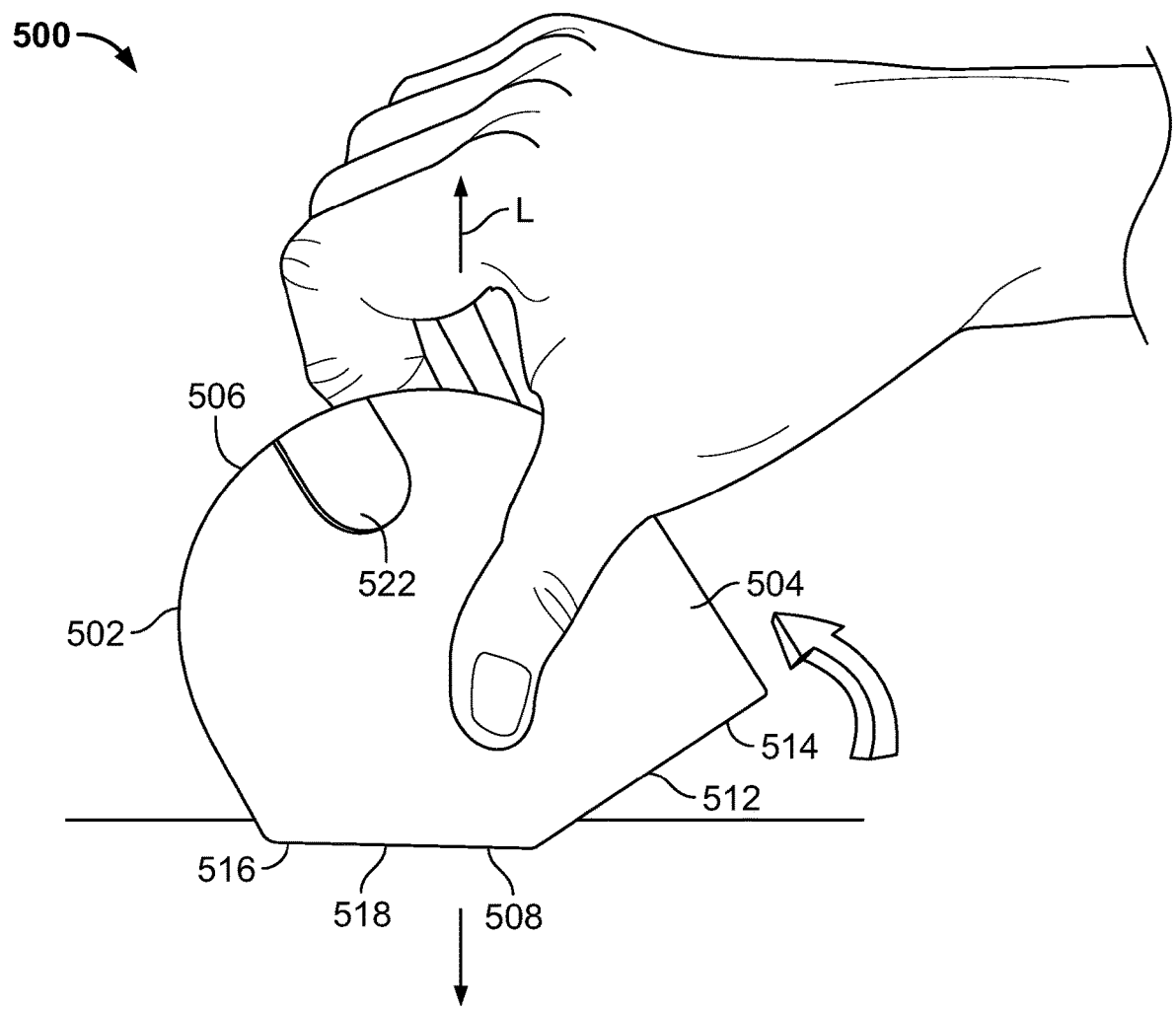
FIG. 14 is a front elevational view of the drug delivery device of FIG. 11 rotated to a use position with a needle shield retracted.

As shown in FIG. 14, to use the device 500, a user positions the base wall 512 of the housing 502 on the skin and pivots the housing 502 about the edge of the mouth 516 defined by the base wall 512. The pivoting action causes the needle guard 524 to contact the skin and pivot or otherwise retract into the housing 502. As the needle guard 524 retracts, the needle is exposed and inserted to a desired subcutaneous depth while the skin contact portion 520 is brought into engagement with the skin. The grip of the retention portion 530 aids a user in holding the device 500 in the desired orientation and location during the injection operation.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various drug delivery devices and methods for use with a drug delivery device. It should be clear that the drug delivery devices or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen®

(epoetin alfa), Aranesp® (darbepoetin alfa), Dynepo® (epoetin delta), Mircera® (methoxy polyethylene glycol-epoetin beta), Hematide®, MRK-2578, INS-22, Retacrit®) (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamoylated erythropoietin, mimetic peptides (including EMP1/hematite), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Figure 4:
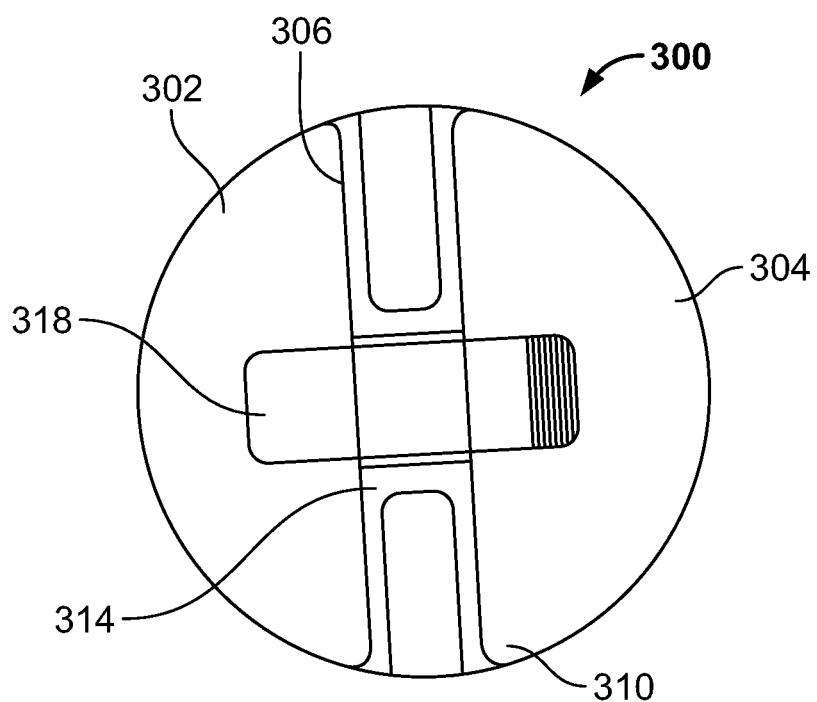
FIG. 4 is a top plan view of the drug delivery device of FIG. 3.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L 1(N); 2×L 1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO: 17 and the light chain of SEQ ID NO: 18; those having the heavy chain variable region of SEQ ID NO:6 and the light chain variable region of SEQ ID NO:8; those having the heavy chain of SEQ ID NO: 19 and the light chain of SEQ ID NO:20; those having the heavy chain variable region of SEQ ID NO: 10 and the light chain variable region of SEQ ID NO: 12; those having the heavy chain of SEQ ID NO:32 and the light chain of SEQ ID NO:20; those having the heavy chain variable region of SEQ ID NO:30 and the light chain variable region of SEQ ID NO: 12; those having the heavy chain sequence of SEQ ID NO:21 and the light chain sequence of SEQ ID NO:22; those having the heavy chain variable region of SEQ ID NO: 14 and the light chain variable region of SEQ ID NO: 16; those having the heavy chain of SEQ ID NO:21 and the light chain of SEQ ID NO:33; and those having the heavy chain variable region of SEQ ID NO: 14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO: 17 as disclosed therein and having a complete light chain of SEQ ID NO: 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL 15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL 12 mAb (ABT-874); anti-IL 12/IL23 mAb (CNTO 1275);

anti-IL 13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
 a housing having a generally vertical orientation along a longitudinal axis;
 drug delivery components disposed within the housing such that at least a plurality of the drug delivery components are disposed in a generally stacked relation along the longitudinal axis, the drug delivery components including a needle;
 a generally planar skin contact surface extending around the needle;
 a retention portion of the skin contact surface configured to grip skin of a user; and
 a needle guard coupled to the housing and movable between a guard position and a use position, the needle guard including a needle opening extending therethrough such that moving the needle guard to the use position causes the needle to extend through the needle opening,
 wherein the needle guard comprises a bottom wall defining at least a portion of the skin contact surface,
 wherein the bottom wall has a dimension extending thereacross that is between about one half and a full height of the housing along the longitudinal axis, such that the housing is stable in a vertical orientation with the housing resting on a horizontal surface.

2. The drug delivery device of claim 1, wherein the bottom wall includes a flange extending outwardly from adjacent portions of the needle guard.

3. The drug delivery device of claim 1, wherein the retention portion comprises an annular retention portion extending around the needle opening.

4. The drug delivery device of claim 1, further comprising a cap including a bottom wall and a sidewall extending upwardly from the bottom wall of the cap, the bottom wall of the cap including a surface configured to engage the retention portion with the cap coupled to at least one of the needle guard or housing and provide a release liner for the retention portion during removal of the cap.

5. The drug delivery device of claim 4, wherein the cap comprises a flexible material and the sidewall includes an inwardly projecting portion configured to engage an edge of the bottom wall of the cap.

6. The drug delivery device of claim 4, wherein the sidewall is sized to extend along the needle guard in a direction generally parallel to the longitudinal axis to engage the housing.

7. The drug delivery device of claim 1, wherein the housing has an inverted frusto-conical configuration with a generally annular cross-section extending perpendicular to the longitudinal axis, a downwardly tapering sidewall, and a top wall.

8. The drug delivery device of claim 1, wherein the housing includes a downwardly oriented housing opening having the needle guard extending therethrough, and the skin contact surface comprises a bottom surface of the housing extending around the housing opening.

9. The drug delivery device of claim 8, wherein the housing further comprises an annular window providing visibility to the drug delivery components disposed within the housing.

10. The drug delivery device of claim 1, wherein the retention portion includes an adhesive layer.

11. A drug delivery device comprising:
a housing having a generally vertical orientation along a longitudinal axis;
drug delivery components disposed within the housing such that at least a plurality of the drug delivery components are disposed in a generally stacked relation along the longitudinal axis, the drug delivery components including a needle;
a generally planar skin contact surface extending around the needle;
a retention portion of the skin contact surface configured to grip skin of a user;
a needle guard coupled to the housing and movable between a guard position and a use position, the needle guard including a needle opening extending therethrough such that moving the needle guard to the use position causes the needle to extend through the needle opening; and
a cap including a bottom wall and a sidewall extending upwardly from the bottom wall, the bottom wall including a surface configured to engage the retention portion with the cap coupled to at least one of the needle guard or housing and provide a release liner for the retention portion during removal of the cap.

12. The drug delivery device of claim 11, wherein the cap comprises a flexible material and the sidewall includes an inwardly projecting portion configured to engage an edge of the bottom wall.

13. The drug delivery device of claim 11, wherein the sidewall is sized to extend along the needle guard in a direction generally parallel to the longitudinal axis to engage the housing.

14. The drug delivery device of claim 11, wherein the needle guard comprises a bottom wall defining at least a portion of the skin contact surface.

15. The drug delivery device of claim 14, wherein the bottom wall of the needle guard has a dimension extending thereacross that is between about one half and a full height of the housing along the longitudinal axis, such that the housing is stable in a vertical orientation with the housing resting on a horizontal surface.

16. The drug delivery device of claim 14, wherein the bottom wall of the needle guard includes a flange extending outwardly from adjacent portions of the needle guard.

17. The drug delivery device of claim 11, wherein the retention portion comprises an annular retention portion extending around the needle opening.

18. The drug delivery device of claim 11, wherein the housing has an inverted frusto-conical configuration with a generally annular cross-section extending perpendicular to the longitudinal axis, a downwardly tapering sidewall, and a top wall.

19. The drug delivery device of claim 11, wherein the housing includes a downwardly oriented housing opening having the needle guard extending therethrough, and the skin contact surface comprises a bottom surface of the housing extending around the housing opening.

20. The drug delivery device of claim 19, wherein the housing further comprises an annular window providing visibility to the drug delivery components disposed within the housing.

* * * * *

UNITED STATES PATENT AND TRADEMARK OFFICE
CERTIFICATE OF CORRECTION

Page 1 of 1

| | |
|---|---|
| PATENT NO. | : 12,115,360 B2 |
| APPLICATION NO. | : 17/256243 |
| DATED | : October 15, 2024 |
| INVENTOR(S) | : Margaux Frances Boyaval et al. |

It is certified that error appears in the above-identified patent and that said Letters Patent is hereby corrected as shown below:

On the Title Page

At Item (57), Line 4, "cep" should be -- cap --.

Signed and Sealed this
Eighteenth Day of November, 2025

John A. Squires
*Director of the United States Patent and Trademark Office*